United States Patent
Huang (10) Patent No.: US 10,980,479 B2
(45) Date of Patent: Apr. 20, 2021

(54) CONTROL METHOD OF WEARABLE DEVICE EXECUTION MODULE AND WEARABLE DEVICE

(71) Applicant: BOE TECHNOLOGY GROUP CO., LTD., Beijing (CN)

(72) Inventor: Zicheng Huang, Beijing (CN)

(73) Assignee: BOE TECHNOLOGY GROUP CO., LTD., Beijing (CN)

(*) Notice: Subject to any disclaimer, the term of this patent is extended or adjusted under 35 U.S.C. 154(b) by 431 days.

(21) Appl. No.: 15/113,160

(22) PCT Filed: Dec. 30, 2015

(86) PCT No.: PCT/CN2015/099773
§ 371 (c)(1),
(2) Date: Jul. 21, 2016

(87) PCT Pub. No.: WO2017/020522
PCT Pub. Date: Feb. 9, 2017

(65) Prior Publication Data
US 2017/0224277 A1    Aug. 10, 2017

(30) Foreign Application Priority Data

Aug. 3, 2015 (CN) .......................... 201510479373.6

(51) Int. Cl.
*A61B 5/00* (2006.01)
*G06F 1/16* (2006.01)
(Continued)

(52) U.S. Cl.
CPC .......... *A61B 5/6801* (2013.01); *A61B 5/0059* (2013.01); *A61B 5/02416* (2013.01);
(Continued)

(58) Field of Classification Search
CPC ..... A61B 5/6801; A61B 5/0059; A61B 5/053; A61B 5/742; A61B 5/6681; A61B 5/7475;
(Continued)

(56) References Cited

U.S. PATENT DOCUMENTS 8,494,507 B1 * 7/2013 Tedesco .................... A61F 4/00
434/112
9,579,060 B1 * 2/2017 Lisy ..................... A61B 5/6803
(Continued)

FOREIGN PATENT DOCUMENTS

CN        101976041 A      2/2011
CN        202235335 U      5/2012
(Continued)

OTHER PUBLICATIONS

First Office Action regarding Chinese Application No. 201510479373.6, dated Apr. 28, 2017. Translation provided by Dragon Intellectual Property Law Firm.
(Continued)

*Primary Examiner* — Gary Jackson
*Assistant Examiner* — Sebastian X Lukjan
(74) *Attorney, Agent, or Firm* — Harness, Dickey & Pierce, P.L.C.

(57) ABSTRACT

The present disclosure discloses a control method of a wearable device execution module and a wearable device. The control method includes detecting at least one touch position and determining a set consisting of the detected at least one touch position as a current touch position set, the at least one touch position being a position at a predetermined touch sensing area; determining an execution module corresponding to the current touch position set as a current execution module based on a correspondence between predetermined touch position sets and execution modules and (Continued)

generating a control command; and transmitting the control command to the current execution module so that the current execution module executes the control command.

5 Claims, 5 Drawing Sheets

(51) Int. Cl.
    *A61B 5/024*     (2006.01)
    *A61B 5/0402*     (2006.01)
    *G06F 3/0488*     (2013.01)
    *A61B 5/11*     (2006.01)
    *A61B 5/053*     (2021.01)

(52) U.S. Cl.
    CPC ............ *A61B 5/0402* (2013.01); *A61B 5/053* (2013.01); *A61B 5/1118* (2013.01); *A61B 5/681* (2013.01); *A61B 5/742* (2013.01); *A61B 5/7475* (2013.01); *G06F 1/163* (2013.01); *G06F 3/0488* (2013.01); *A61B 2562/0219* (2013.01)

(58) Field of Classification Search
    CPC . A61B 5/1118; A61B 5/0402; A61B 5/02416; A61B 2562/0219; G06F 3/0416; G06F 1/163; G06F 3/0488
    See application file for complete search history.

(56) References Cited

U.S. PATENT DOCUMENTS

| | | | |
|---|---|---|---|
| 2009/0278806 A1* | 11/2009 | Duarte | G06F 3/0416 345/173 |
| 2010/0041965 A1* | 2/2010 | Kang | A61B 5/00 600/301 |
| 2012/0016210 A1* | 1/2012 | Kim | A61B 5/02416 600/301 |
| 2013/0235704 A1 | 9/2013 | Grinberg | |
| 2014/0358012 A1* | 12/2014 | Richards | A61B 5/4812 600/479 |
| 2015/0135310 A1* | 5/2015 | Lee | A61B 5/681 726/20 |
| 2016/0239142 A1* | 8/2016 | Kim | G06F 3/0488 |
| 2017/0127966 A1* | 5/2017 | Wu | A61B 5/0402 |

FOREIGN PATENT DOCUMENTS

| | | |
|---|---|---|
| CN | 102681727 A | 9/2012 |
| CN | 102937869 A | 2/2013 |
| CN | 203166860 U | 8/2013 |
| CN | 203693576 U | 7/2014 |
| CN | 104298400 A | 1/2015 |
| CN | 104598071 A | 5/2015 |
| CN | 105030204 A | 11/2015 |

OTHER PUBLICATIONS

International Search Report and Written Opinion of the International Searching Authority for International Application No. PCT/CN2015/099773, dated Apr. 27, 2016. Translation provided by Dragon Intellectual Property Law Firm.

Third Chinese Office Action regarding Application No. 201510479373.6 dated Dec. 5, 2017. English translation provided by http://globaldossier.uspto.gov.

Second Chinese Office Action regarding Application No. 201510479373.6 dated Sep. 13, 2017. English translation provided by http://globaldossier.uspto.gov.

* cited by examiner

CONTROL METHOD OF WEARABLE DEVICE EXECUTION MODULE AND WEARABLE DEVICE

CROSS-REFERENCE TO RELATED APPLICATION

This application is the U.S. national phase of PCT Application No. PCT/CN2015/099773 filed on Dec. 30, 2015, which claims a priority of the Chinese Patent Application No. 201510479373.6 filed on Aug. 3, 2015, the disclosures of which are incorporated in their entirety by reference herein.

TECHNICAL FIELD

The present disclosure relates to the field of medical technology, in particular to a control method of a wearable device execution module and a wearable device.

BACKGROUND

Along with the rapid development of social economy and social growth of the aging population, people pay more attention to their health. Wearable devices which can easily detect the health condition at any time become the urgent needs of society. The current wearable device is configured to measure only a single physiological parameter (such as pulse rate). When a plurality of physiological parameters (such as pulse rate and blood pressure) needs to be detected, a user needs to use different kinds of wearable devices to detect the different physiological parameters. This may degrade user's convenience for operation, and thus cause, to the user, inconvenience in portable performance and operation performance.

SUMMARY

An object of the present disclosure is to provide a control method of the wearable device execution module and a wearable device so as to improve the user experience.

According to an aspect, the present disclosure provides a control method of a wearable device execution module. The control method includes detecting at least one touch position and determining a set consisting of the detected at least one touch position as a current touch position set, the at least one touch position being a position at a predetermined touch sensing area; determining an execution module corresponding to the current touch position set as a current execution module based on a correspondence between predetermined touch position sets and execution modules and generating a control command; and transmitting the control command to the current execution module so that the current execution module executes the control command.

Optionally, the step of determining of the execution module corresponding to the current touch position set as the current execution module based on the correspondence between the predetermined touch position sets and the execution modules and generating a control command includes: in the case that the detected touch positions include only a first touch position and a second touch position, determining a first detector corresponding to the predetermined touch position set consisting of only the first touch position and the second touch position as the current execution module; in the case that the detected touch positions include only the second touch position and a third touch position, determining a second detector corresponding to the predetermined touch position set consisting of only the second touch position and the third touch position as the current execution module; and in the case that the detected touch positions include the first touch position, the second touch position, and the third touch position, determining the first detector and the second detector corresponding to the predetermined touch position set consisting of the first touch position, the second touch position, and the third touch position as the current execution module.

Optionally, the control method further includes: receiving, from a terminal, a correspondence between the predetermined touch position sets and the execution modules; and updating the correspondence that is pre-stored with the received correspondence.

Optionally, there are at least two predetermined touch sensing areas and the predetermined touch position set consists of at least two touch positions.

Optionally, the first detector is configured to measure routine activity parameters and includes an acceleration sensor and a photoelectric sensor, and the second detector is configured to measure health related parameters and includes a photoelectric sensor and two electrodes.

In another aspect, the present disclosure provides a wearable device. The wearable device includes: a detection module configured to detect at least one touch position and determine a set consisting of the detected at least one touch position as a current touch position set, the at least one touch position being a position at a predetermined touch sensing area; a determination module configured to determine an execution module corresponding to the current touch position set as a current execution module based on a correspondence between predetermined touch position sets and execution modules and generate a control command; and execution modules configured to receive the control command transmitted from the determination module and execute the control command.

Optionally, the determination module is configured to in the case that the detected touch positions include only a first touch position and a second touch position, determine a first detector corresponding to the predetermined touch position set consisting of only the first touch position and the second touch position as the current execution module; in the case that the detected touch positions include only the second touch position and a third touch position, determine a second detector corresponding to the predetermined touch position set consisting of only the second touch position and the third touch position as the current execution module; and in the case that the detected touch positions include the first touch position, the second touch position, and the third touch position, determine the first detector and the second detector corresponding to the predetermined touch position set consisting of the first touch position, the second touch position, and the third touch position as the current execution module.

Optionally, the detection module includes a metal plate, at least two metal blocks positioned on one side of the metal plate, and at least two thermal sensors positioned on the other side of the metal plate and corresponding to the at least two metal blocks, respectively.

Alternatively, the detection module includes three metal blocks positioned on one side of the metal plate.

Alternatively, the predetermined touch position set consists of at least two of the three metal blocks.

Optionally, the wearable device further includes: a communication module configured to receive, from a terminal, the correspondence between the predetermined touch position sets and the execution modules; and an update module configured to update the correspondence that is pre-stored with the received correspondence.

Optionally, the execution module includes an acceleration sensor, an optical sensor, and two electrodes for detecting an electric potential difference between two different body parts of a user, and the acceleration sensor, the optical sensor, and the two electrodes are respectively connected to the determination module.

According to the embodiments of the present disclosure, the following advantages will be provided.

By detecting at least one touch position and determining a set consisting of the detected touch positions as a current touch position set, determining an execution module corresponding to the current touch position set as a current execution module based on a correspondence between the predetermined touch position sets and execution modules and generating a control command; and transmitting the control command to the current execution module so that the current execution module executes the control command, it is able to perform the detection with different execution module by using fingers to touch different positions, thereby to obtain different physiological parameters and it is able to detect multiple kinds of physiological parameters by a single wearable device, which improves the operation convenience for the user, and improves the portable performance of the device.

BRIEF DESCRIPTION OF THE DRAWINGS

In order to describe the technical solution according to embodiments of the present disclosure more clearly, the following will describe the drawings used for the embodiments of the present disclosure. It should be understood that the following described drawings are only a part of embodiments of the present disclosure. For a person skilled in the art, other drawings can be obtained without paying creative effort.

FIG. 6A to FIG. 6E are diagrams showing an example of the wearable device according to an embodiment of the present disclosure.

DETAILED DESCRIPTION

The technical solution according to embodiments of the present disclosure will be described in detail below with reference to the accompanying drawings.

Unless otherwise defined, any technical or scientific terms used herein shall have the common meaning understood by a person of ordinary skills. Such words as "first" and "second" used in the specification and claims are merely used to differentiate different components rather than to represent any order, number or importance. Similarly, such words as "one" or "one of" are merely used to represent the existence of at least one member, rather than to limit the number thereof. Such words as "connect" or "connected to" may include electrical connection, direct or indirect, rather than being limited to physical or mechanical connection. Such words as "on/above", "under/below", "left" and "right" are merely used to represent relative position relationship, and when an absolute position of an object is changed, the relative position relationship will be changed too.

Figure 1:
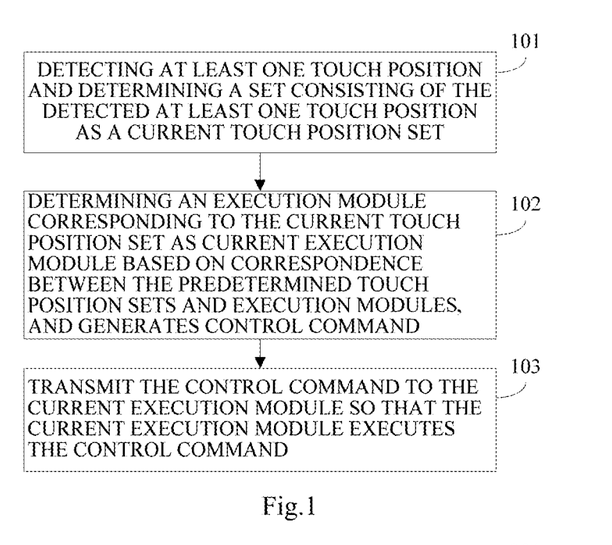
FIG. 1 is a flowchart showing a control method of a wearable device execution module according an embodiment of the present disclosure.

An embodiment of the present disclosure provides a control method of a wearable device execution module. Refer to FIG. 1, the control method includes step 101, step 102, and step 103.

Step 101: detecting at least one touch position and determining a set consisting of the detected at least one touch position as a current touch position set.

In a practical application, a wearable device, such as a wrist-watch, a wristband, a pair of smart glasses, can detect a touch position where a body part of a user is touched on a touch screen of the wearable device.

The touch position is a position at a predetermined touch sensing area.

Alternatively, the number of the predetermined touch sensing areas may be one, two or more.

For example, the number of the predetermined touch sensing areas may be three. The three predetermined touch sensing areas include a predetermined touch sensing area 1, a predetermined touch sensing area 2, and a predetermined touch sensing area 3. The position at the predetermined touch sensing area 1 is a touch position 1, the position at the predetermined touch sensing area 2 is a touch position 2, and the position at the predetermined touch sensing area 3 is a touch position 3.

In a practical application, the touch position set consisting of different touch positions may be pre-defined as a predetermined touch position set.

For example, with taking the touch position 1, the touch position 2, and the touch position 3 as an example, a touch position set consisting of only the touch position 1 may be defined as a predetermined touch position set 1, a touch position set consisting of only the touch position 2 may be defined as a predetermined touch position set 2, and a touch position set consisting of only the touch position 3 may be defined as a predetermined touch position set 3.

In another example, a touch position set consisting of only the touch position 1 and the touch position 2 may be defined as a predetermined touch position set 1, a touch position set consisting of only the touch position 1 and the touch position 3 may be defined as a predetermined touch position set 2, and a touch position set consisting of only the touch position 2 and the touch position 3 may be defined as a predetermined touch position set 3.

In another example, a touch position set consisting of only the touch position 1 may be defined as a predetermined touch position set 1, a touch position set consisting of only the touch position 1 and the touch position 2 may be defined as a predetermined touch position set 2, and a touch position set consisting of the touch position 1, the touch position 2, and the touch position 3 may be defined as a predetermined touch position set 3. Above are only some examples of the present disclosure, and the present disclosure is not limited thereto.

Step 102: determining an execution module corresponding to the current touch position set as a current execution module based on a correspondence between the predetermined touch position sets and execution modules, and generating a control command.

For example, for the predetermined touch position set 1, the predetermined touch position set 2, and the predetermined touch position set 3, the predetermined touch position set 1 corresponds to a detector 1 of the execution module, the predetermined touch position set 2 corresponds to a detector 2 of the execution module, the predetermined touch position set 3 corresponds to both the detector 1 and the detector 2 of the execution module. These correspondences may be pre-stored in a storage device of the wearable device.

In the case that the current touch position set is the predetermined touch position set 1, the current execution module only includes the detector 1. In the case that the current touch position set is the predetermined touch position set 2, the current execution module only includes the detector 2. In the case that the current touch position set is the predetermined touch position set 3, the current execution module includes detector 1 and the detector 2.

The control command may be a command of turning on, turning off, or suspending/pausing, which may be pre-set.

Step 103: transmitting the control command to the current execution module so that the current execution module executes the control command.

Suppose that the control command is a command of turning on.

In the case that the current execution module includes only the detector 1, the control command is transmitted only to the detector 1 so that the detector 1 executes the control command. In the case that the current execution module includes only the detector 2, the control command is transmitted only to the detector 2 so that the detector 2 executes the control command. In the case that the current execution module includes the detector 1 and the detector 2, the control command is transmitted to both the detector 1 and the detector 2 at the same time so that the detector 1 and the detector 2 execute the turn-on command and activate their detection functions.

In an embodiment of the present disclosure, the control method includes detecting at least one touch position and determining a set consisting of the detected touch positions as a current touch position set, determining the execution module corresponding to the current touch position set as a current execution module based on a correspondence between predetermined touch position sets and execution modules and generating a control command; and transmitting the control command to the current execution module so that the current execution module executes the control command Therefore, it is able to perform the detection with different execution modules by using fingers to touch different positions, thereby to obtain different physiological parameters and it is able to detect multiple kinds of physiological parameters by a single wearable device, which improves the operation convenience for the user, and improves the portable performance of the device.

Further, when fingers touch different positions, different execution modules are activated to detect the touch operation so as to obtain different physiological parameters. That is, by switching the finger touch position, the detector corresponding to the finger touch position is switched and activated. This improves an operation performance and further improves convenience for the user operation.

Figure 2:
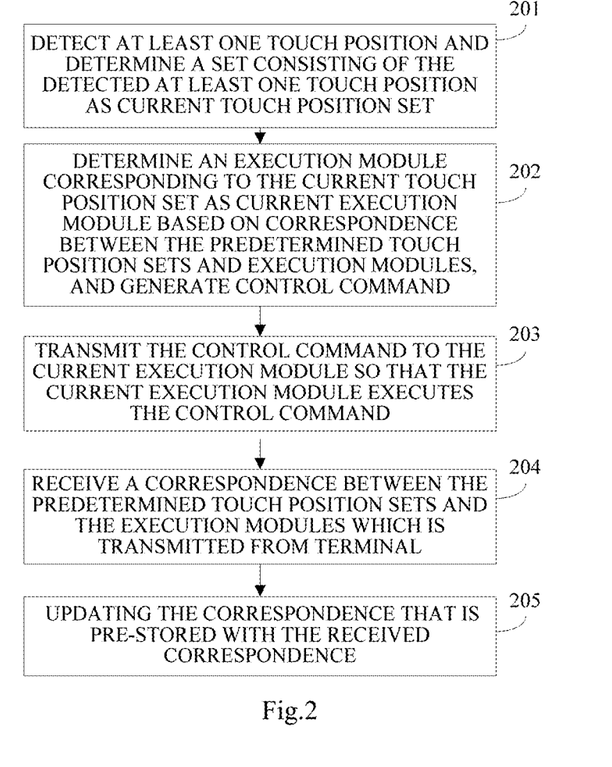
FIG. 2 is another flowchart showing the control method of a wearable device execution module according an embodiment of the present disclosure.

The present disclosure further provides in some embodiment a control method of a wearable device execution module. Refer to FIG. 2. The control method includes step 201, step 202, step 203, step 204, and step 205.

Step 201: detecting at least one touch position and determine a set consisting of the detected touch positions as a current touch position set. Herein, the touch position is a position at a predetermined touch sensing area.

Alternatively, the number of the predetermined touch sensing areas may be at least two. For example, in the case that the number of the predetermined touch sensing areas is three, three predetermined touch sensing areas include a predetermined touch sensing area 1, a predetermined touch sensing area 2, and a predetermined touch sensing area 3. A position at the predetermined touch sensing area 1 is a touch position 1, a position at the predetermined touch sensing area 2 is a touch position 2, and a position at the predetermined touch sensing area 3 is a touch position 3.

In a practical application, a touch position set consisting of different touch positions may be pre-set as the predetermined touch position set.

For example, for the touch position 1, the touch position 2, and the touch position 3, a touch position set consisting of only the touch position 1 may be defined as the predetermined touch position set 1, a touch position set consisting of only the touch position 2 may be defined as the predetermined touch position set 2, a touch position set consisting of only the touch position 3 may be defined as the predetermined touch position set 3. In another example, a touch position set consisting of only the touch position 1 and the touch position 2 may be defined as the predetermined touch position set 1, a touch position set consisting of only the touch position 1 and the touch position 3 may be defined as the predetermined touch position set 2, and a touch position set consisting of only the touch position 2 and the touch position 3 may be defined as the predetermined touch position set 3. In another example, a touch position set consisting of only the touch position 1 may be defined as the predetermined touch position set 1, a touch position set consisting of only the touch position 1 and the touch position 2 may be defined as the predetermined touch position set 2, and a touch position set consisting of the touch position 1, the touch position 2, and the touch position 3 may be defined as the predetermined touch position set 3. In the present disclosure, the determining of the predetermined touch position set is not limited to the above-described examples.

Step 202: determining an execution module corresponding to the current touch position set as a current execution module based on a correspondence between predetermined touch position sets and execution modules, and generating a control command.

For example, for the predetermined touch position set 1, the predetermined touch position set 2, and the predetermined touch position set 3, the predetermined touch position set 1 may correspond to a detector 1 of the execution module, the predetermined touch position set 2 may correspond to a detector 2 of the execution module, and the predetermined touch position set 3 may correspond to the detector 1 and the detector 2 of the execution module. In the case that the current touch position set is the predetermined touch position set 1, the current execution module includes only the detector 1. In the case that the current touch position set is the predetermined touch position set 2, the current execution module includes only the detector 2. In the case that the current touch position set is the predetermined touch position set 3, the current execution module includes the detector 1 and the detector 2.

Alternatively, the predetermined touch position set may include at least two touch positions.

It should be understood that, the touch position set includes at least two touch positions. In this configuration, only when the two touch positions are touched at a same time, the detection is activated. Thus, even when only one touch position is touched accidentally, the detection is not activated and this configuration improves a controlling accuracy.

In an embodiment of the present embodiment, the step 202 may include: in the case that the detected touch positions include only the first touch position and the second touch position, determining the first detector corresponding to the predetermined touch position set consisting of only the first touch position and the second touch position as the current execution module; in the case that the detected touch positions include only the second touch position and the third touch position, determining the second detector corresponding to the predetermined touch position set consisting of only the second touch position and the third touch position as current execution module; and in the case that the detected touch positions include the first touch position, the second touch position, and the third touch position, determining the first detector and the second detector corresponding to the predetermined touch position set consisting of the first touch position, the second touch position, and the third touch position as the current execution module.

The first detector may be partially or entirely different from the second detector. Specifically, the first detector and the second detector may be defined based on the detection parameters. For example, the first detector may be used to detect routine activity parameters (such as movement parameters and sleeping parameters). The first detector may include an acceleration sensor and a photoelectric sensor. The second detector may be used to detect health related parameters (such as pulse rate, heart rate, and blood pressure). The second detector may include a photoelectric sensor and two electrodes. In this case, the first detector is partially different from the second detector.

For example, in the case that the detected touch positions include only the first touch position and the second touch position, the acceleration sensor detects the movement parameters and the photoelectric sensor detects sleeping parameters. In the case that the detected touch positions include only the second touch position and the third touch position, the photoelectric sensor detects the pulse rate and the blood pressure, and the two electrodes detect the heart rate. In the case that the detected touch positions include the first touch position, the second touch position, and the third touch position, the acceleration sensor detects the movement parameters, the photoelectric sensor detects the sleeping parameters, pulse rate, and the blood pressure, and the two electrodes detect the heart rate.

Understandably, the number of the detectors included in the current execution module may be set corresponding to the number of the detected touch positions. For example, in the case that all of the touch positions (the first touch position, the second touch position, and the third touch position) are detected, the current execution module includes all of the detectors (the first detector and the second detector). This configuration helps the user to remember the usage.

In a practical application, the acceleration sensor may be configured to detect a movement state of the user. The optical sensor is configured to emit an optical signal to body's tissues, receives the reflected optical signal by the body's tissue, and converts the received signal into at least one of the pulse rate, blood pressure information, or respiratory rate. The pulse rate and the blood pressure indicate a health condition of the user, and the respiratory rate indicates a sleeping condition of the user. The two electrodes are configured to detect a potential difference between two body parts, obtain electrocardiography based on the potential difference, and obtain a heart rate of the user.

Step 203: transmitting the control command to the current execution module so that the current execution module executes the control command.

For example, for the detector 1 and the detector 2, in the case that the current execution module includes only the detector 1, the control command is transmitted only to the detector 1 so that the detector 1 executes the control command. In the case that the current execution module includes only the detector 2, the control command is transmitted only to the detector 2 so that the detector 2 executes the control command. In the case that the current execution module includes the detector 1 and the detector 2, the control command is transmitted at the same time to both the detector 1 and the detector 2 so that both the detector 1 and the detector 2 execute the control command.

Step 204: receiving the correspondence between the predetermined touch position sets and the execution modules which is transmitted from a terminal.

Step 205, updating the correspondence that is pre-stored with the received correspondence.

For example, it may be supposed that, in the pre-stored correspondence, the predetermined touch position set 1 corresponds to the detector 1 of the execution module, the predetermined touch position set 2 corresponds to the detector 2 of the execution module, and the predetermined touch position set 3 corresponds to both the detector 1 and the detector 2 of the execution module. Herein, the predetermined touch position set 1 includes only the touch position 1 and the touch position 2, the predetermined touch position set 2 includes only the touch position 2 and the touch position 3, and the predetermined touch position set 3 includes the touch position 1, the touch position 2, and the touch position 3.

When the user feels the pre-stored correspondence is complicated to operate and wants to change the correspondence in such a manner that a predetermined touch position set 4 corresponds to the detector 1 of the execution module, a predetermined touch position set 5 corresponds to the detector 2 of the execution module, and a predetermined touch position set 6 corresponds to the detector 1 and the detector 2 of the execution module. Herein, the predetermined touch position set 4 includes only the touch position 1, the predetermined touch position set 5 includes only the touch position 3, and the predetermined touch position set 6 includes only the touch position 2. In this case, the changed correspondence may be transmitted to the wearable device by the terminal for changing the correspondence.

By the step 204 and step 205, the correspondence between the predetermined touch position sets and the execution modules can be changed. Thus, the correspondence between the predetermined touch position sets and the execution modules can be changed according to a user's habit and this can improve user experience.

It should be noted that step 204 and step 205 are optional steps, and there is no defined execution order with steps 201 to 203.

In the embodiment of the present disclosure, by detecting at least one touch position and determining a set consisting of the detected touch position as a current touch position set, determining an execution module corresponding to the current touch position set as a current execution module based on a correspondence between predetermined touch position sets and execution modules and generating a control command; and transmitting the control command to the current execution module so that the current execution module executes the control command, it is able to perform the detection with different execution modules by using fingers to touch different positions, thereby to obtain different physiological parameters and it is able to detect multiple kinds of physiological parameters by a single wearable device, which improves the operation convenience for the user, and improves the portable performance of the device.

Figure 3:
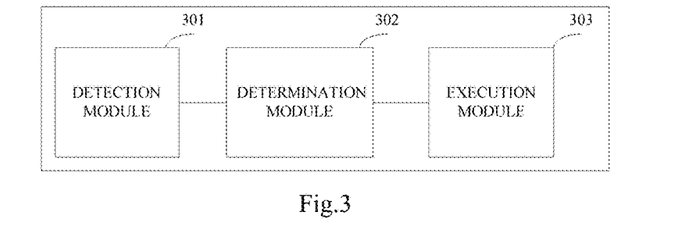
FIG. 3 is a block diagram showing a configuration of a wearable device according an embodiment of the present disclosure.

Refer to FIG. 3, the present disclosure provides in an embodiment a wearable device. The wearable device includes: a detection module 301 configured to detect at least one touch position and determine a set consisting of the detected at least one touch position as a current touch position set, the at least one touch position being a position at a predetermined touch sensing area; a determination module 302 configured to determine an execution module corresponding to the current touch position set as a current execution module based on a correspondence between predetermined touch position sets and execution modules and generating a control command; and execution modules 303 receiving a control command transmitted from the determination module 302 and executing the control command.

In the embodiment of the present disclosure, by detecting, using the detection module, at least one touch position and determining a set consisting of the detected touch positions as a current touch position set, determining, using the determination module, an execution module corresponding to the current touch position set as a current execution module based on a correspondence between predetermined touch position sets and execution modules and generating a control command; and receiving, by the execution module, the control command from the determination module and executing the control command, it is able to perform the detection with different execution modules by using fingers to touch different positions, thereby to obtain different physiological parameters and it is able to detect multiple kinds of physiological parameters by a single wearable device, which improves the operation convenience for the user, and improves the portable performance of the device.

Figure 4:
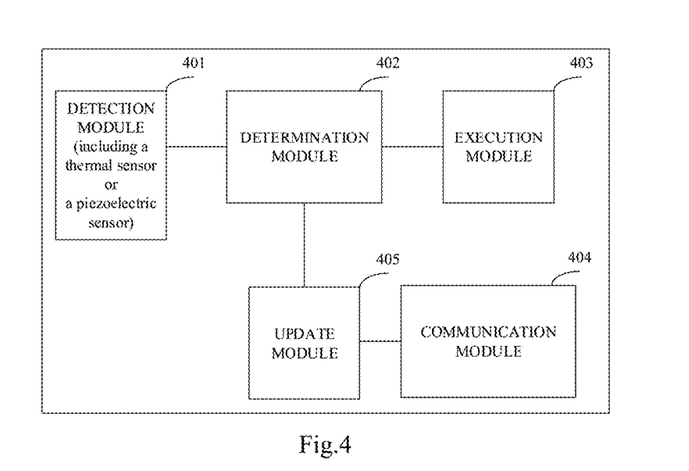
FIG. 4 is another block diagram showing a configuration of a wearable device according an embodiment of the present disclosure.

Refer to FIG. 4, the present disclosure further provides in an embodiment a wearable device. The wearable device includes: a detection module 401 configured to detect at least one touch position and determine a set consisting of the detected touch position as a current touch position set, the at least one touch position being a position at a predetermined touch sensing area; a determination module 402 configured to determine an execution module corresponding to the current touch position set as a current execution module based on a correspondence between predetermined touch position sets and execution modules and generating a control command; and execution modules 403 receiving a control command transmitted from the determination module 402 and executing the control command.

The wearable device may be a wrist-watch.

In an embodiment of the present disclosure, the predetermined touch position set may include at least two touch positions.

Alternatively, the determination module 402 may be configured as follows.

In the case that the detected touch positions include only the first touch position and the second touch position, the determination module determines the first detector corresponding to the predetermined touch position set consisting of only the first touch position and the second touch position as the current execution module.

In the case that the detected touch positions include only the second touch position and the third touch position, the determination module determines the second detector corresponding to the predetermined touch position set consisting of only the second touch position and the third touch position as the current execution module.

In the case that the detected touch positions include the first touch position, the second touch position, and the third touch position, the determination module determines the first detector and the second detector corresponding to the predetermined touch position set consisting of the first touch position, the second touch position, and the third touch position as the current execution module.

The first detector may be partially or entirely different from the second detector. Specifically, the first detector and the second detector may be defined based on the detection parameters. For example, the first detector may be used to detect routine activity parameters (such as movement parameters and sleeping parameters). The first detector may include an acceleration sensor and a photoelectric sensor. The second detector may be used to detect health related parameters (such as pulse rate, heart rate, and blood pressure). The second detector may include a photoelectric sensor and two electrodes. In this case, the first detector is partially different from the second detector.

Figure 5:
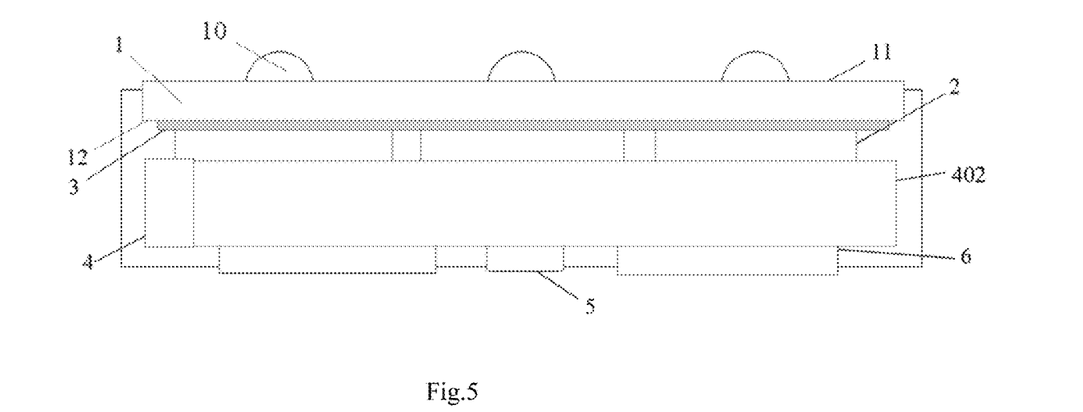
FIG. 5 is a block diagram showing configurations of an input module and an execution module according to an embodiment of the present disclosure.

In an embodiment of the present disclosure, as shown in FIG. 5, the detection module 401 may include a metal plate 1. On one side of the metal plate 1, at least two metal blocks 10 are positioned, and on the other side of the metal plate 1, at least two thermal sensors 2 are positioned corresponding to the at least two metal blocks 10, respectively.

Understandably, the detection module is achieved using the thermal sensor of the metal plate, and this achieves a low manufacturing cost.

Alternatively, as shown in FIG. 5, the thermal sensor 2 may be attached to one side of the metal plate using insulating thermal conductive adhesive 3.

Understandably, the insulating thermal conductive adhesive can avoid an interference generation caused by an electrical signal when the user touches on the metal plate using a finger. Thus, the insulating thermal conductive adhesive can improve controlling accuracy.

Alternatively, as shown in FIG. 5, three metal blocks 10 may be positioned on one side of the metal plate 1.

Understandably, by the three metal blocks, detection can be activated only when the fingers touch at least two positions. With this configuration, when only one touch position is touched accidentally by a finger, the detection is not activated and this configuration improves a controlling accuracy.

Optionally, the predetermined touch position set may include at least two of the three metal blocks 10.

Figure 6A:
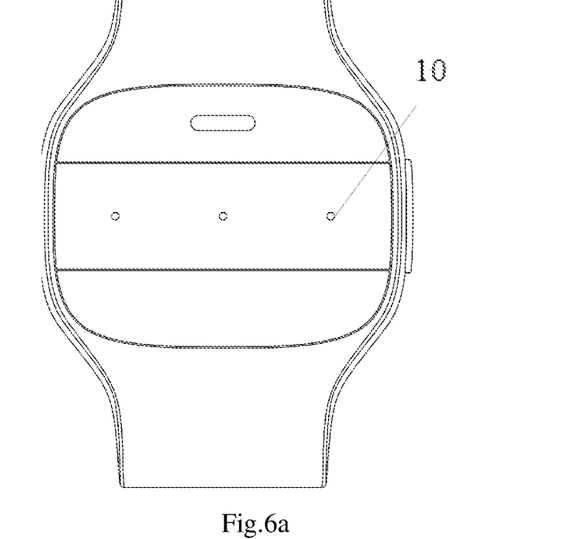
Figure 6B:
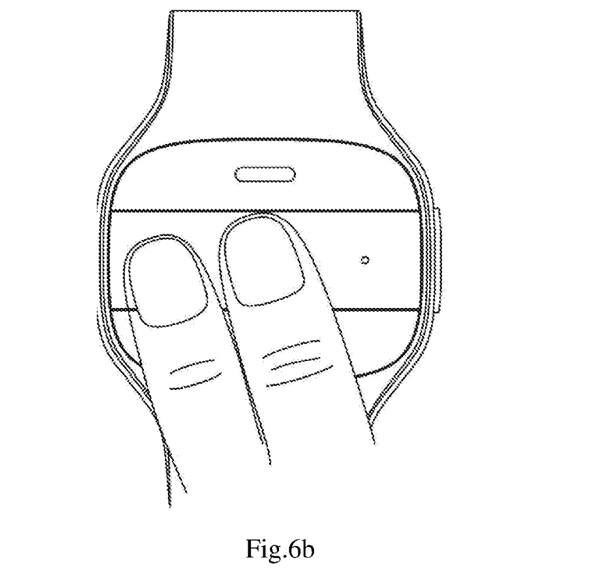
Figure 6C:
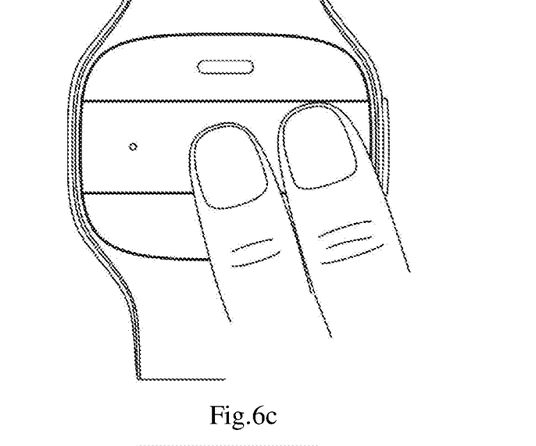
Figure 6D:
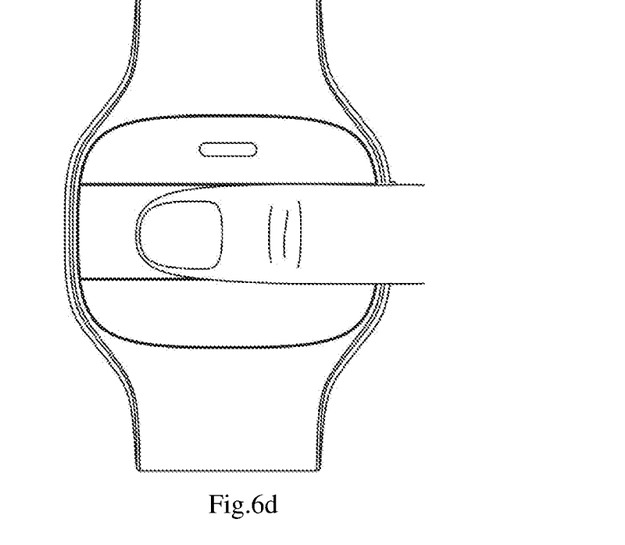

For example, as shown in FIG. 6a, the wearable device includes three metal blocks 10. The three metal blocks 10 correspond to the first touch position, the second touch position, and the third touch position. As shown in FIG. 6b, when the user touches two metal blocks 10 at the left side, the current touch position set consists of only the first touch position and the second touch position, and the current execution module includes only the first detector. As shown in FIG. 6c, when the user touches two metal blocks 10 at the right side, the current touch position set consists of only the second touch position and the third touch position, and the current execution module includes only the second detector. As shown in FIG. 6d, when the user touches the three metal blocks 10, the current touch position set consists of the first touch position, the second touch position, and the third touch position, and the current execution module includes the first detector and the second detector.

In other embodiments, the detection module 401 may include a touch panel. A predetermined area on the touch panel is defined as the touch position. The detection module 401 may further include some piezoelectric sensors. In this case, one piezoelectric sensor corresponds to one touch position.

In an embodiment of the present disclosure, the wearable device further includes a communication module 404 configured to receive, from a terminal, a correspondence between the predetermined touch position sets and the execution modules; and an update module 405 configured to update the correspondence that is pre-stored with the received correspondence.

Understandably, the communication module changes the correspondence between the predetermined touch position sets and the execution modules. Thus, the correspondence between the predetermined touch position sets and the execution modules can be changed according to a user's habit and this can improve user experience.

In an embodiment of the present disclosure, as shown in FIG. 5, the execution module 403 may include an acceleration sensor 4, an optical sensor 5, and two electrodes 6. The acceleration sensor 4, the optical sensor 5, and two electrodes 6 are connected to the determination module 402.

It is easy to understand that the acceleration sensor is configured to detect the movement state of the user. The optical sensor is configured to emit an optical signal to body's tissues, receives a reflected optical signal by the body's tissue, and converts the received signal into at least one of the pulse rate, blood pressure information, or respiratory rate. The pulse rate and the blood pressure may indicate a health condition of the user, and the respiratory rate indicates a sleeping condition of the user. The two electrodes are configured to detect a potential difference between two body parts, such as limbs, obtain electrocardiography based on the potential difference, and obtain a heart rate of the user.

Understandably, the execution module can be achieved by adopting the acceleration sensor, the optical sensor, and the two electrodes, which may have a low manufacturing cost.

Figure 6E:
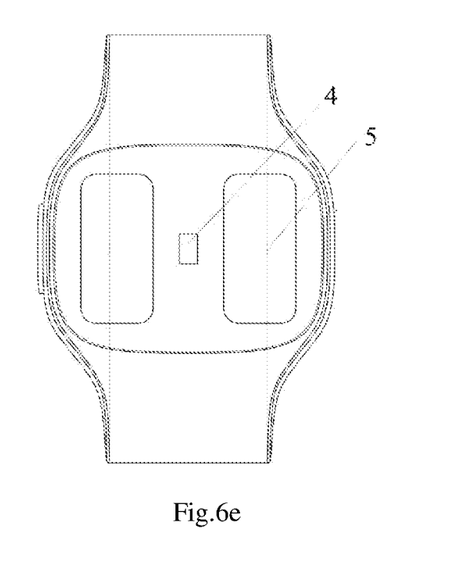

Alternatively, as shown in FIG. 6e, a distance between the two electrodes 6 may be larger than a predetermined distance.

It is easy to understand that detection of the heart rate is achieved by detecting an electrical potential difference between two body parts of the user. Thus, the further the distance between the two electrodes, the larger the electrical potential difference and the more accurate detection result. Therefore, when the distance between the two electrodes 6 is larger than the predetermined distance, the detection accuracy can be improved.

Optionally, the optical sensor 5 may be positioned between the two electrodes 6 in order to reduce a dimension of the wearable device and improves the portable performance.

Alternatively, the two electrodes may be metal electrodes.

Understandably, a conductivity of metal is higher than nonmetal and has a higher detection performance in detection of the potential difference of the user. Thus, the detection accuracy can be improved.

In the embodiment of the present disclosure, by detecting, using the detection module, at least one touch position and determining a set consisting of the detected touch position as a current touch position set, determining, using the determination module, an execution module corresponding to the current touch position set as a current execution module based on a correspondence between predetermined touch position sets and execution modules and generating a control command; and receiving, by the execution module, the control command from the determination module and executing the control command, it is able to perform the detection with different execution modules by using fingers to touch different positions, thereby to obtain different physiological parameters and it is able to detect multiple kinds of physiological parameters by a single wearable device, which improves the operation convenience for the user, and improves the portable performance of the device.

The above are merely the preferred embodiments of the present disclosure and the present disclosure is not limited to the above-described embodiments. It should be understood that modifications, changes and improvements made without departing from the spirit and principle of the present disclosure shall also fall within the scope of the present disclosure.

What is claimed is:

1. A wearable device comprising:
a metal plate, wherein a metal block is arranged on one side of the metal plate, and a thermal sensor or a piezoelectric sensor is arranged on the other side of the metal plate, the metal plate with the thermal sensor or the piezoelectric sensor is configured to detect at least two touch positions touched by user at a same time and determine a set comprising at least two detected touch positions as a current touch position set, wherein the at least two touch positions are positioned at predetermined touch sensing areas, there are at least two predetermined touch sensing areas and a predetermined touch position set comprising at least three predetermined touch positions, and the metal plate with the thermal sensor or the piezoelectric sensor is further configured to form a plurality of predetermined touch position sets in accordance with a plurality of combinations of the predetermined touch sensing areas;
an acceleration sensor, an optical sensor and two electrodes, wherein different combinations of at least two of the acceleration sensor, the optical sensor and both the two electrodes respectively correspond to different predetermined touch position sets; in accordance with the current touch position set detected by the metal plate, the combination of at least two of the acceleration sensor, the optical sensor and the two electrodes, corresponding to the current touch position set, is configured to perform detection;
a determination module configured to determine the combinations of at least two of the acceleration sensor, the optical sensor and both the two electrodes corresponding to the current touch position set.

2. The wearable device according to claim 1, wherein at least two metal blocks positioned on one side of the metal plate, and at least two thermal sensors positioned on the other side of the metal plate and corresponding to the at least two metal blocks, respectively.

3. The wearable device according to claim 2, wherein three metal blocks are positioned on one side of the metal plate.

4. The wearable device according to claim 3, wherein the predetermined touch position set comprises at least two of the three metal blocks.

5. The wearable device according to claim 1, wherein the two electrodes are configured to detect an electric potential difference between two different body parts of a user.

* * * * *